US012667287B2

(12) United States Patent
Li et al.

(10) Patent No.: US 12,667,287 B2
(45) Date of Patent: Jun. 30, 2026

(54) COMPACT IMPLANTABLE BIOSENSOR ASSEMBLY AND BIOLOGICAL INFORMATION MONITORING DEVICE

(71) Applicant: Shenzhen Refresh Biosensing Technology Co., Ltd., Shenzhen (CN)

(72) Inventors: Guanhua Li, Shenzhen (CN); Qianghua Li, Shenzhen (CN); Dan Yan, Shenzhen (CN); Zhe Zhang, Shenzhen (CN); Qinglong Dong, Shenzhen (CN); Qing Li, Shenzhen (CN)

(73) Assignee: Shenzhen Refresh Biosensing Technology Co., Ltd., Shenzhen (CN)

( * ) Notice: Subject to any disclaimer, the term of this patent is extended or adjusted under 35 U.S.C. 154(b) by 545 days.

(21) Appl. No.: 18/143,602

(22) Filed: May 4, 2023

(65) Prior Publication Data

US 2024/0032830 A1     Feb. 1, 2024

(30) Foreign Application Priority Data

Jul. 30, 2022     (CN) .......................... 202210912591.4

(51) Int. Cl.
 *A61B 5/1486* (2006.01)
 *A61B 5/00* (2006.01)
(52) U.S. Cl.
 CPC ........ *A61B 5/14865* (2013.01); *A61B 5/0031* (2013.01); *A61B 5/6846* (2013.01)

(58) Field of Classification Search
 CPC ........... A61B 2560/045; A61B 5/0031; A61B 5/14503; A61B 5/14532; A61B 5/14865; A61B 5/6846; A61B 5/6848
 See application file for complete search history.

(56) References Cited

U.S. PATENT DOCUMENTS

| | | | |
|---|---|---|---|
| 7,381,184 B2 * | 6/2008 | Funderburk ....... | A61B 5/14503 604/59 |
| 2016/0058474 A1 * | 3/2016 | Peterson ................ | A61B 5/686 600/347 |
| 2022/0202366 A1 * | 6/2022 | Mitchell ................... | C08F 2/48 |
| 2022/0257153 A1 * | 8/2022 | Jeong ................. | A61B 5/14503 |
| 2022/0265210 A1 * | 8/2022 | Cargill ............... | A61B 5/14532 |
| 2025/0098991 A1 * | 3/2025 | Cho ..................... | A61B 5/6849 |
| 2025/0221636 A1 * | 7/2025 | Mitchell ............ | A61B 5/14532 |

* cited by examiner

*Primary Examiner* — Eric J Messersmith

(57) ABSTRACT

The invention discloses a compact implantable biosensor assembly and a biological information monitoring device containing the assembly. The lower part of the implanted sensing section and of the needled for implantation are sealed in a closed space formed by the barrier, the lower part of the enclosure and the lower part of the needle aid. The horizontal connection section of the implantable sensing electrode is embedded in the enclosure. The export electrode is used to connect with a transmitter. The implantable biosensor assembly is directly connected with the circuit board of the transmitter through the export electrode, whereby the structure is compact.

12 Claims, 8 Drawing Sheets

COMPACT IMPLANTABLE BIOSENSOR ASSEMBLY AND BIOLOGICAL INFORMATION MONITORING DEVICE

CROSS REFERENCE TO RELATED APPLICATIONS

The present application claims the benefit of Chinese Patent Application No. 202210912591.4 filed on Jul. 30, 2022, the contents of which are incorporated herein by reference in their entirety.

TECHNICAL FIELD

The invention relates to the technical field of biological information monitoring, in particular to a compact implantable biosensor assembly and a biological information monitoring device.

BACKGROUND ART

For people with diabetes, the traditional fingertip glucometer has such shortcomings as being invasive, providing limited information, and being unable to reflect blood glucose fluctuations and provide early warning, so it cannot meet the needs of some people, especially type 1 diabetes patients who need real-time transmission of blood glucose fluctuations and type 2 diabetes patients who need intensive insulin treatment.

To meet the need for continuous blood glucose monitoring, it is necessary to use the integrated implantable assembly and internal components of an implantable biosensor to implant the sensor into the subcutaneous tissue of the human body to measure the blood glucose concentration between tissue fluids, which is a means of continuous monitoring that can be employed in reality. The single service life of the implantable biosensor is one to two weeks, which greatly reduces the pain caused by continuous fingertip blood sampling and venous blood sampling. At present, such implantable devices on the market have problems such as complex user operation, long implantation process, and easiness to trigger the push device by mistake, which reduces the user compliance (patient compliance/treatment compliance refers to the extent to which a patient follows medical advice and instructions for their treatment, and is also called patient "cooperation"; otherwise, it is called non-compliance) and degrades the user experience.

In the prior art, the small size of the transmitter (the device used to transmit the monitored biological signal) helps to improve the wearing experience. In the current integrated products, the transmitter is in the working or silent state when it is placed in the injector. However, no matter which way, the transmitter and the sensor assembly have already been electrically connected. Due to the small size of the transmitter, the size of the battery is limited, leading to a small battery capacity. The hardware must have an extremely low power consumption to meet the requirements for the shelf life of the product (shelf life is the guarantee of and commitment to the quality and efficacy of a commodity in the circulation period).

In the current integrated products, the transmitter and implantable sensing electrode are integrated. After production and before implantation into the human body, disinfection and sterilization are required. Disinfection and sterilization require a relatively large packaging box, which occupies a relatively large space and leads to a high cost.

At present, there is no technical solution in the industry where the implantable sensing electrode and the transmitter circuit board are split.

SUMMARY OF THE INVENTION

In view of the above, the present invention provides a compact implantable biosensor assembly, which has a small sterile unit and does not consume or consumes a tiny amount of electricity before implantation into the human body.

A compact implantable biosensor assembly, comprising an enclosure, an implantable sensing electrode, a needle aid and a barrier;

the implantable sensing electrode comprises a first wide vertical section, a horizontal connection section and an implanted sensing section; the two sides of the horizontal connection section are respectively connected with the lower end of the first wide vertical section and the upper end of the implanted sensing section; the surface of the first wide vertical section is provided with an export electrode; the needle aid comprises a needle seat and a needle for implantation;

the lower part of the implanted sensing section and of the needle for implantation are sealed in a closed space formed by the barrier, the lower part of the enclosure and the lower part of the needle aid; the horizontal connection section of the implantable sensing electrode is embedded in the enclosure;

the export electrode is exposed on the surface of the enclosure, and is used to connect with a transmitter; or the export electrode is exposed on the bottom surface of the upper counterbore of the enclosure, and is used to connect with a transmitter;

the enclosure is provided with an assembly structure for engaging with the transmitter.

Preferably, the horizontal connection section comprises a first horizontal flat section and an upwardly bending connection section connected with each other;

the left side of the first horizontal flat section is connected to the lower part of the right side of the first wide vertical section, and the upwardly bending connection section is connected to the left side of the implanted sensing section near the upper end.

Preferably, the upper right end of the implanted sensing section is provided with a bump; or the right upper end of the implanted sensing section has no bump, and the part where the needle for implantation contacts the right upper end of the implanted sensing section is provided with a pressure contact bump.

Preferably, the section of the puncture part of the needle for implantation is C-shaped $\sqsubset$-shaped. After assembly, the implanted sensing section is contained inside the C-shape or in the recess of th $\sqsubset$-shape.

The upper right end of the implanted sensing section is provided with a bump, which is pressed against the inner wall of the needle for implantation so as to deform the implanted sensing section with the upwardly bending connection section as the fulcrum; the lower end of the implanted sensing section is contained inside the C-shape or in the recess of th $\sqsubset$-shape of the needle for implantation and would not stick out of the lower end of the needle for implantation; or the pressure contact bump is pressed against the upper right end of the implanted sensing section so as to deform the implanted sensing section with the upwardly bending connection section as the fulcrum; the lower end of the implanted sensing section is contained inside the C-shape or in the recess of th⸛⸛ -shape of the needle for implantation and would not stick out of the lower end of the needle for implantation.

Preferably the enclosure comprises an upper housing and a lower housing, and the lower housing covers the lower part of the upper housing;

the upper housing is provided with a needle aid guide hole and an electrode guide slot; the needle aid guide hole and the electrode guide slot are in communication in the lower part of the upper housing; and the needle for implantation passes through the needle aid guide hole from the upper part of the needle aid guide hole and sticks out downward; the needle aid guide hole is arranged beside the lower housing;

the electrode guide slot penetrates the upper housing, wherein its lower section is narrow, and its upper section is provided with a counterbore and is a wide structure;

the horizontal part of the implantable sensing electrode extends out from the needle aid guide hole, passes through the junction between the lower housing and the upper housing and enters the space between the lower housing and the upper housing; the first wide vertical section passes through the electrode guide slot from the lower part of the electrode guide slot and sticks out upward; the electrode guide slot is narrow in the lower part and wide in the upper part; the width of the narrow lower part is 0.1~0.3 mm larger than the thickness of the first vertical section of the electrode, for glue sealing; the upper wide part provides space for the bent part of the connector or connecting sheet, and its size is adapted to the connector or connecting sheet fitted on the transmitter; the lower part of the first vertical section of the implantable sensing electrode and the lower narrow section of the electrode guide slot are sealed by glue to form a sealed structure; the lower part of the first vertical section of the electrode is provided with a through-hole structure or a toothed edge structure, which is used for reliable bonding and sealing with glue.

The horizontal part of the implantable sensing electrode is sealed with glue at the junction between the lower housing and the upper housing. The first wide vertical section and the lower narrow part of the electrode guide slot are sealed with glue.

The function of the electrode guide slot comprises the guidance of the electrode, sealing of the sterile airtight cavity, and the upper counterbore's avoidance of the connector and elastic sheet, etc.

Preferably, the lower part of the upper housing is provided with a recessed edge; part of the recessed edge is provided with a deep glue-dispensing sub-slot; the upper part of the lower housing is provided with a protruding edge, and the protruding edge is provided with two adjacent engagement protuberances;

sealing glue is provided in the recessed edge and the glue-dispensing sub-slot; the two engagement protuberances are inserted into the glue-dispensing sub-slot; the horizontal part of the implantable sensing electrode passes between the two engagement protuberances; the protruding edge is clamped into the recessed edge; after the sealing glue is solidified, the horizontal part of the implantable sensing electrode is sealed by the sealing glue at the junction of the lower housing and the upper housing, and the lower housing and the upper housing are sealed.

Preferably, the needle aid guide hole is provided with three steps; the upper step is in the upper part of the upper housing, and the lower step is in the lower part of the upper housing; the lower parts of the upper step and of the middle step are circular holes respectively; the step surface of the circular hole of the middle step is provided with a first seal ring, and at the bottom of the lower step is a notched arched hole;

the lower part of the needle seat is provided with an arched section with an opening which is adapted to the notched arched hole; above the arched section with an opening is a part adapted to the seal ring; the part adapted to the seal ring is sleeved inside the first seal ring; above the part adapted to the seal ring is a vertical guide part; the vertical guide part is adapted to and clearance fits with the circular hole in the lower part of the upper step surface; above the vertical guide part is an upper boss; the bottom surface of the upper boss is on the top surface of the upper step.

The invention also provides a biological information monitoring device.

A biological information monitoring device, comprising a transmitter and a compact implantable biosensor assembly;

the transmitter is provided with an assembly through-hole; the compact implantable biosensor assembly detachably passes through the assembly through-hole and is engaged with the assembly through-hole; the transmitter is provided with a main control circuit board; the main control circuit board is provided with an electrode through-hole; the upper part of the first wide vertical section passes through or approaches the electrode through-hole; a signal input and output end of the main control circuit board is in communication with the export electrode.

For the structure of the compact implantable biosensor assembly, please see the above description. It comprises an enclosure, an implantable sensing electrode, a needle aid and a barrier.

The implantable sensing electrode comprises a first wide vertical section, a horizontal connection section, and an implanted sensing section. The two sides of the horizontal connection section are respectively connected with the lower end of the first wide vertical section and the upper end of the implanted sensing section. The surface of the first wide vertical section is provided with an export electrode. The needle aid comprises a needle seat, and a needle for implantation.

The lower part of the implanted sensing section and of the needle for implantation are sealed in a closed space formed by the barrier, the lower section of the enclosure and the lower section of the needle aid. The horizontal connection section of the implantable sensing electrode is embedded in the enclosure.

The export electrode is exposed on the surface of the enclosure, and the export electrode is used to connect with the transmitter; or the export electrode is exposed on the bottom surface of the upper counterbore on the enclosure, and the export electrode is used to connect with a transmitter.

The enclosure is provided with an assembly structure for engaging with the transmitter.

Preferably, the horizontal connection section comprises a first horizontal flat section and an upwardly bending connection section which are connected with each other.

The left side of the first horizontal flat section is connected to the lower section of the right side of the first wide vertical section, and the upwardly bending connection section is connected to the left side of the implanted sensing segment near the upper end.

Preferably, the upper right end of the implanted sensing section is provided with a bump; or there is no bump at the upper right end of the implanted sensing section, and a pressure contact bump is provided in the part where the needle for implantation contacts the upper right end of the implanted sensing section.

Preferably, the section of the puncture part of the needle for implantation is C-shaped or 凵-shaped. After assembly, the implanted sensing segment is contained inside the C-shape or in the recess in the 凵-shape.

The upper right end of the implanted sensing section is provided with a bump, which is pressed against the inner wall of the needle for implantation so as to deform the implanted sensing section with the upwardly bending connection section as the fulcrum; the lower end of the implanted sensing section is contained inside the C-shape or in the recess in the 凵-shape of the needle for implantation and would not stick out of the lower end of the needle for implantation; or the pressure contact bump is pressed against the upper right end of the implanted sensing section so as to deform the implanted sensing section with the upwardly bending connection section as the fulcrum; the lower end of the implanted sensing section is contained inside the C-shape or in the recess in the 凵-shape of the needle for implantation and would not stick out of the lower end of the needle for implantation.

Preferably, the enclosure comprises an upper housing and a lower housing. The lower housing covers the bottom of the upper housing.

The upper housing is provided with a needle aid guide hole and an electrode guide slot. The needle for implantation passes through the needle aid guide hole from the upper part of the needle aid guide hole and sticks out downward. The needle aid guide hole is arranged beside the lower housing.

The electrode guide slot penetrates the upper housing, wherein its lower section is narrow, and its upper section is provided with a counterbore and is a wide structure.

The horizontal part of the implantable sensing electrode extends out from the needle aid guide hole, passes through the junction between the lower housing and the upper housing and enters the space between the lower housing and the upper housing. The first wide vertical section passes through the electrode guide slot from the lower part of the electrode guide slot and sticks out upward.

The horizontal part of the implantable sensing electrode is sealed with glue at the junction between the lower housing and the upper housing.

The function of the electrode guide slot comprises the guidance of the electrode, sealing of the sterile airtight cavity, and the upper counterbore's avoidance of the connector and elastic sheet, etc.

Preferably, the lower part of the upper housing is provided with a recessed edge. Part of the recessed edge is provided with a deep glue-dispensing sub-slot. The upper part of the lower housing is provided with a protruding edge, and the protruding edge is provided with two adjacent engagement protuberances.

Sealing glue is provided in the recessed edge and the glue-dispensing sub-slot. The two engagement protuberances are inserted into the glue-dispensing sub-slot. The horizontal part of the implantable sensing electrode passes between the two engagement protuberances. The protruding edge is clamped into the recessed edge. After the sealing glue is solidified, the horizontal part of the implantable sensing electrode is sealed by the sealing glue at the junction of the lower housing and the upper housing, and the lower housing and the upper housing are sealed.

Preferably, the needle aid guide hole is provided with three steps. The lower parts of the upper step and of the middle step are circular holes respectively. The step surface of the circular hole of the middle step is provided with a first seal ring, and at the bottom of the lower step is a notched arched hole.

The lower part of the needle seat is provided with an arched section with an opening which is adapted to the notched arched hole. Above the arched section with an opening is a part adapted to the seal ring. The part adapted to the seal ring is sleeved inside the first seal ring. Above the part adapted to the seal ring is a vertical guide part. The vertical guide part is adapted to and clearance fits with the circular hole in the lower part of the upper step surface. Above the vertical guide part is an upper boss. The bottom surface of the upper boss is on the top surface of the upper step.

Preferably, it also includes connector, part of which is connected to the main control circuit board; or the connector is integrally formed with the main control circuit through FPC flexible board process or rigid-flexible combined board process.

The connector is provided with a plurality of first contacts, which are arranged on the left and right sides. The gap distance between the first contacts arranged on both sides is less than the thickness of the first wide vertical section. The first contacts are arranged on the electrode through-hole.

The first wide vertical section passes through the gap between the first contacts arranged on both sides. The first contacts arranged on both sides squeeze the first wide vertical section from both sides. At least part of the first contacts squeezes the export electrode. The export electrode is electrically connected to the signal input and output end of the main control circuit board through the first contacts.

The first contacts will be squeezed and deformed, and the first wide vertical section will also be squeezed and slightly deformed, realizing the signal communication between the transmitter and the compact implantable biosensor assembly.

Preferably, the first contacts arranged on both sides are symmetrically arranged on both sides; or the first contacts arranged on both sides are staggered on both sides.

Compared with the first contacts arranged symmetrically, the first contacts staggered on both sides may be longer, the gap between the two sides is smaller, the bending of the first contacts is longer after the first wide vertical section is inserted into the gap, and the contact (point contact, line contact or surface contact) between the first contacts and the export electrode is more reliable.

Preferably, it further includes a connecting sheet.

There are two or more connecting sheets. One end of the connecting sheets is connected to the main control circuit board, and the other end of the connecting sheets is pressed against the surface of the export electrode.

The connecting sheets have certain rigidity and elasticity, such as bending a copper sheet, stainless steel sheet, etc. into the shape of an elastic sheet. The first wide vertical section sticks out from a side of the connecting sheets or from the gap between the connecting sheets on both sides. The connecting sheets can effectively squeeze or clamp the export electrode. The elasticity and rigidity of the connecting sheets make the connection at the connection point between the connecting sheets 02 and the export electrode more reliable.

In order to facilitate welding, the surface of the conductive part of the connecting sheets or connectors needs to have a weldable plating, such as nickel, gold, etc. In order to ensure welding consistency, the welding end at the end of the connectors will be welded through the through-hole of the weld leg of the main control circuit board, and the welding end of the plane is welded with the surface welding point of the main control circuit board.

Preferably, while the compact implantable biosensor assembly engages with the assembly through-hole, the spring pin provided on the enclosure is inserted into the power switch hole of the transmitter.

In the initial state, the conductive material on the inner wall of the power switch hole is divided into a left semicircle and a right semicircle. The left semicircle and the right semicircle are completely disconnected. After the spring pin is inserted into the power switch hole, the spring pin is compressed and reliably connects the left semicircle and the right semicircle, realizing the electrification of the entire system circuit.

The spring pin may also be other equivalent conductors.

Preferably, the surface of the first wide vertical section on both sides is provided with an export electrode. There are three or more export electrodes.

The two sides of the implanted sensing section are provided with a working electrode, a reference electrode and a counter electrode. There are three or more export electrodes. The working electrode, reference electrode and counter electrode are connected respectively with different export electrodes through the lines of the implantable sensing electrode. The working electrode, reference electrode and counter electrode are connected with the signal input and output end of the main control circuit board through the export electrodes respectively.

The beneficial effects of the invention are as follows: the invention discloses a compact implantable biosensor assembly and a biological information monitoring device containing the assembly. It comprises an enclosure, an implantable sensing electrode, a needle aid and a barrier. The implantable sensing electrode comprises a first wide vertical section, a horizontal connection section and an implanted sensing section, and the surface of the first wide vertical section is provided with an export electrode. The needle aid comprises a needle seat and a needle for implantation. The lower part of the implanted sensing section and of the needled for implantation are sealed in a closed space formed by the barrier, the lower part of the enclosure and the lower part of the needle aid. The horizontal connection section of the implantable sensing electrode is embedded in the enclosure. The export electrode is exposed on the surface of the enclosure, and is used to connect with a transmitter; or the export electrode is exposed on the bottom surface of the upper counterbore of the enclosure, and is used to connect with a transmitter. The enclosure is provided with an assembly structure for engaging with the transmitter. The implantable biosensor assembly is directly connected with the circuit board of the transmitter through the export electrode, whereby the structure is compact.

BRIEF DESCRIPTION OF THE DRAWINGS

The following is a further description of a compact implantable biosensor assembly of the invention in combination with the drawings.

IN THE FIGURES

1—Enclosure; 11—Upper housing; 110—Assembly structure; 111—Recessed edge; 1111—Glue-dispensing sub-slot; 118—Needle aid guide hole; 1183—Notched arched hole; 119—Electrode guide slot; 12—Lower housing; 121—Protruding edge; 1211—Engagement protuberance; 15—Spring pin; 3—Implantable sensing electrode; 31—A first wide vertical section; 311—Export electrode; 32—Horizontal connection section; 321—First horizontal flat section; 322—Upwardly bending connection section; 33—Implanted sensing section; 331—Bump; 4—Needle aid; 40—Needle seat; 401—Arched section with an opening; 402—Part adapted to the seal ring; 403—Vertical guide part; 405—Upper boss; 43—Needle for implantation; 431—Pressure contact bump; 6—Barrier; 10—Transmitter; 102—Assembly through-hole; 101—Main control circuit board; 1011—Electrode through-hole; 103—Power switch hole; 01—Connector; 011—First contact; 02—Connecting sheet; 031—First seal ring

DETAILED DESCRIPTION OF THE DRAWINGS

Figure 1:
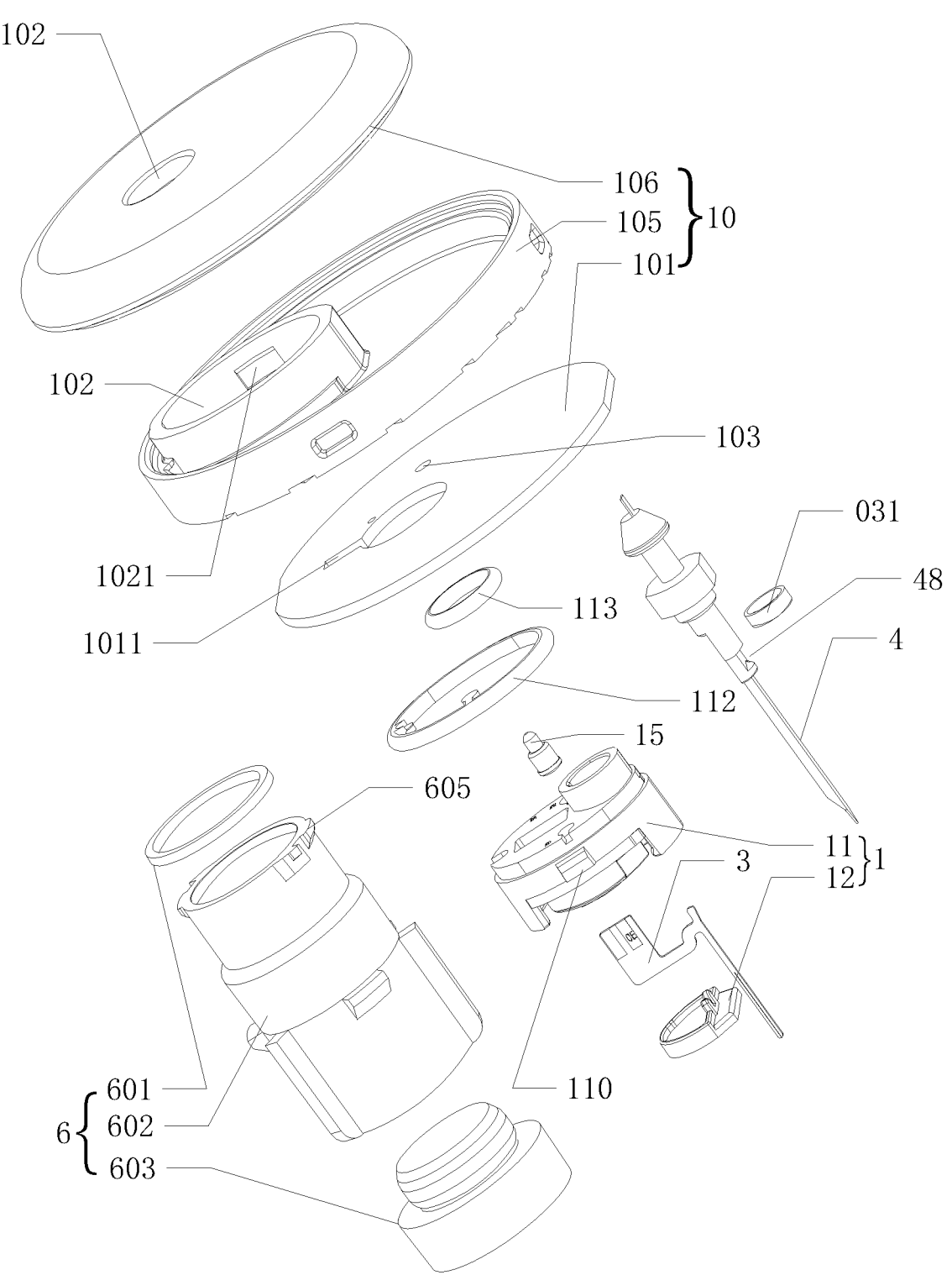
FIG. 1 is a structural breakdown diagram of a biological information monitoring device of the invention, including a barrier.
Figure 2:
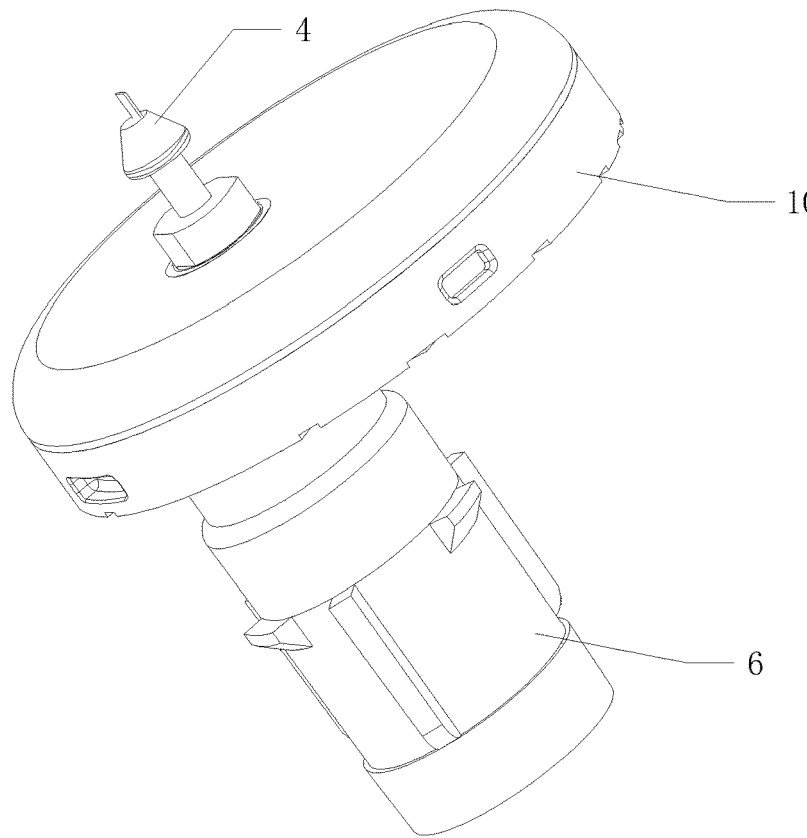
FIG. 2 is a structural diagram of a biological information monitoring device of the invention before use, including a barrier.
Figure 3:
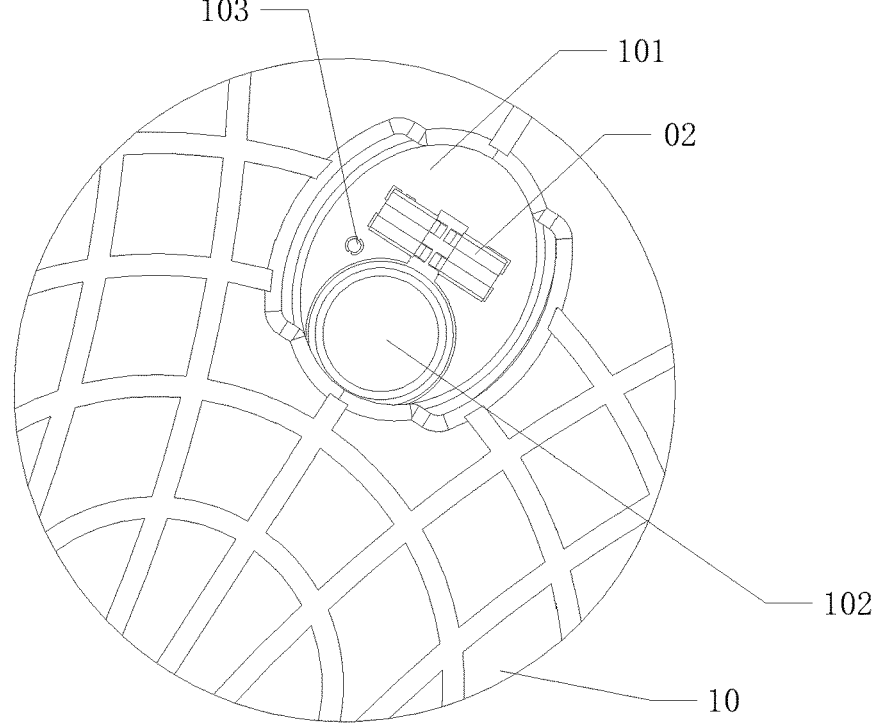
FIG. 3 is a structural diagram of the bottom of a transmitter of a biological information monitoring device of the invention.
Figure 4:
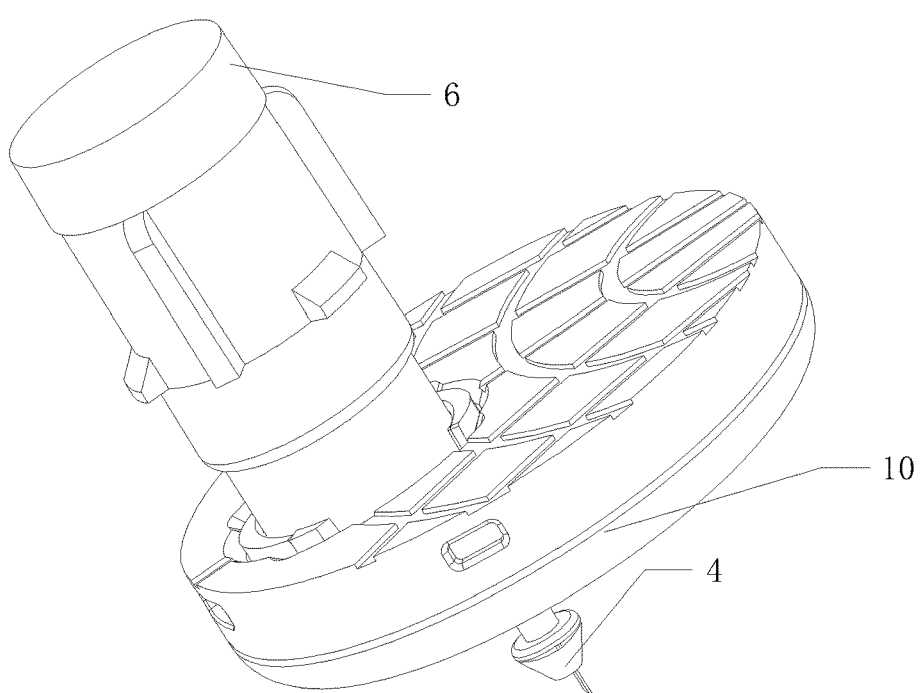
FIG. 4 is a structural diagram of the bottom perspective of a biological information monitoring device of the invention before use, including a barrier.
Figure 5:
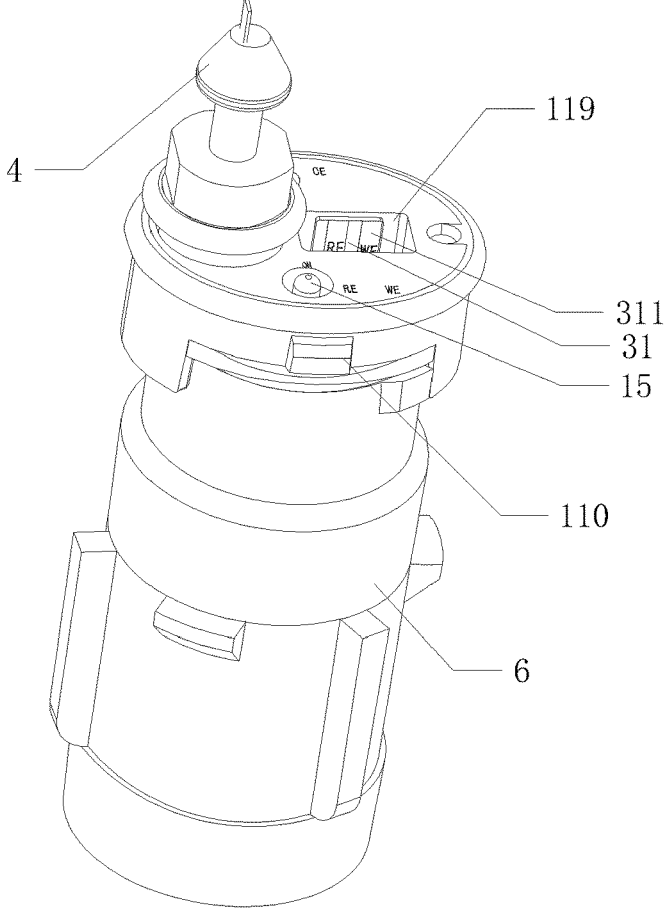
FIG. 5 is an assembly diagram of a compact implantable biosensor assembly of the invention, including a barrier.
Figure 6:
FIG. 6 is a structural diagram of the bottom of a circuit board of an embodiment of a biological information monitoring device of the invention.
Figure 6:
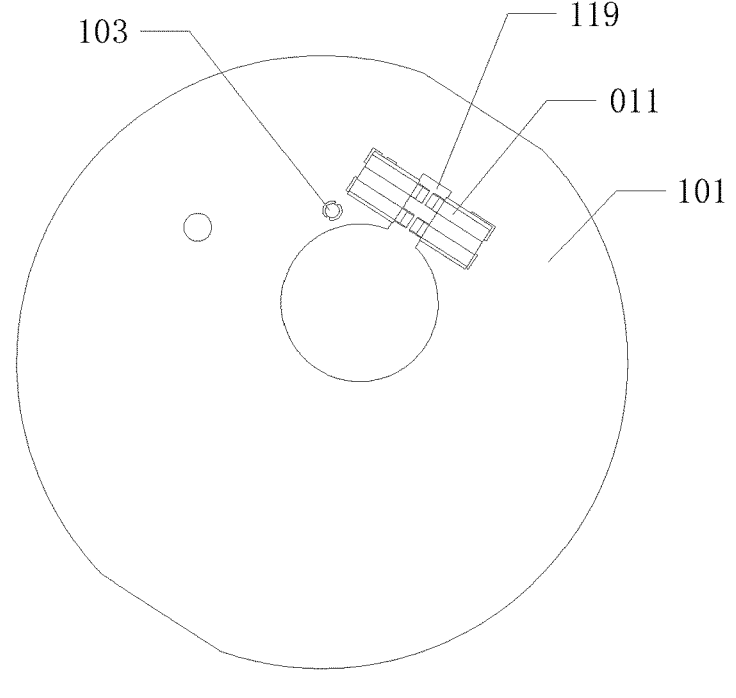
Figure 7:
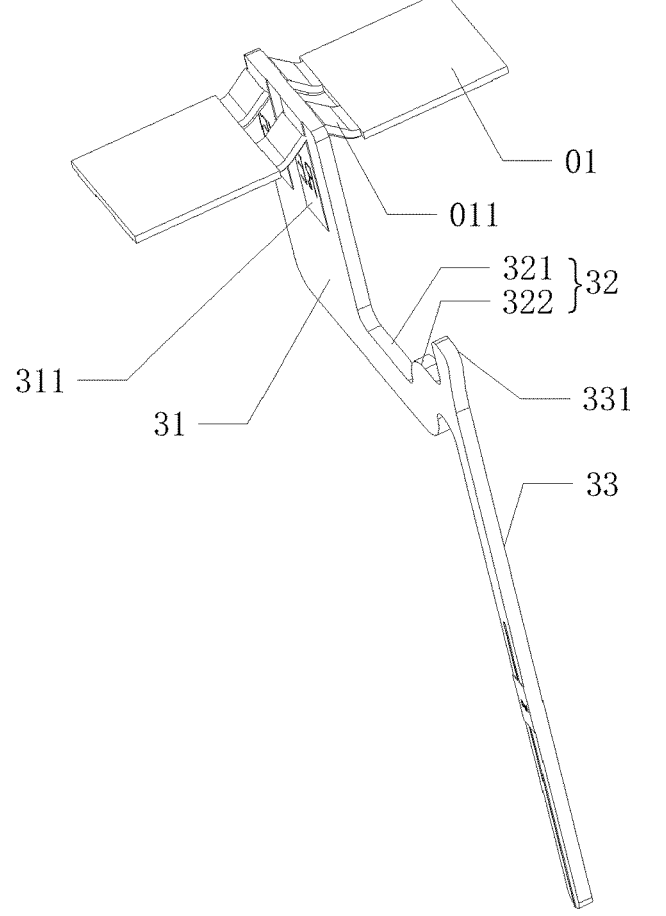
FIG. 7 is a structural diagram of an implantable sensing electrode fitting with a connector in an embodiment of a biological information monitoring device of the invention.
Figure 8:
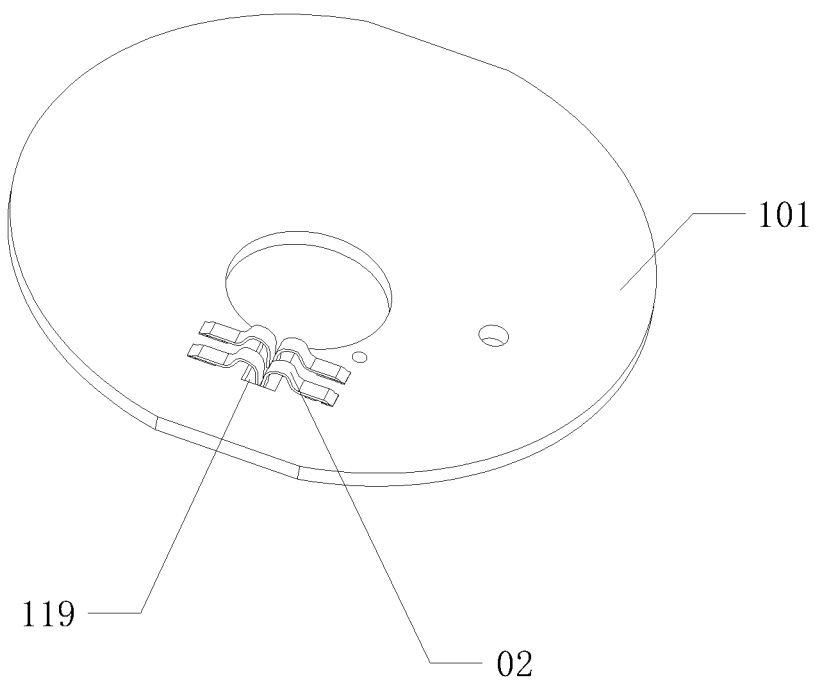
FIG. 8 is a structural diagram of a circuit board in another embodiment of a biological information monitoring device of the invention, wherein the connecting sheet is made of a rigid and elastic metal sheet.
Figure 9:
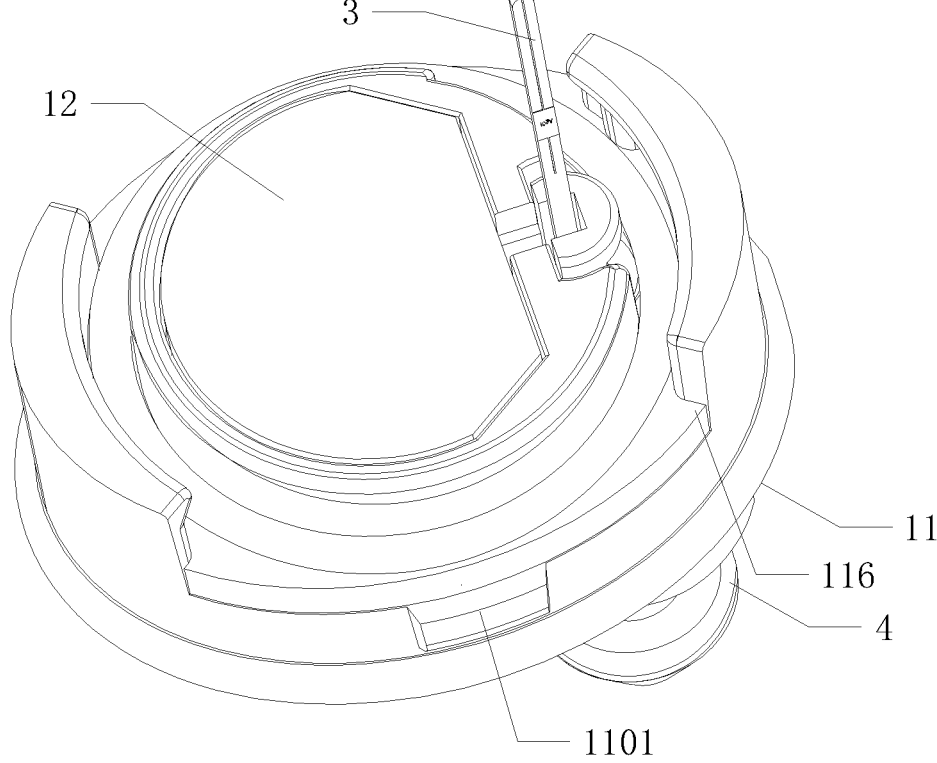
FIG. 9 is a structural diagram of a perspective of a compact implantable biosensor assembly of the invention, with the needle for implantation being removed.
Figure 10:
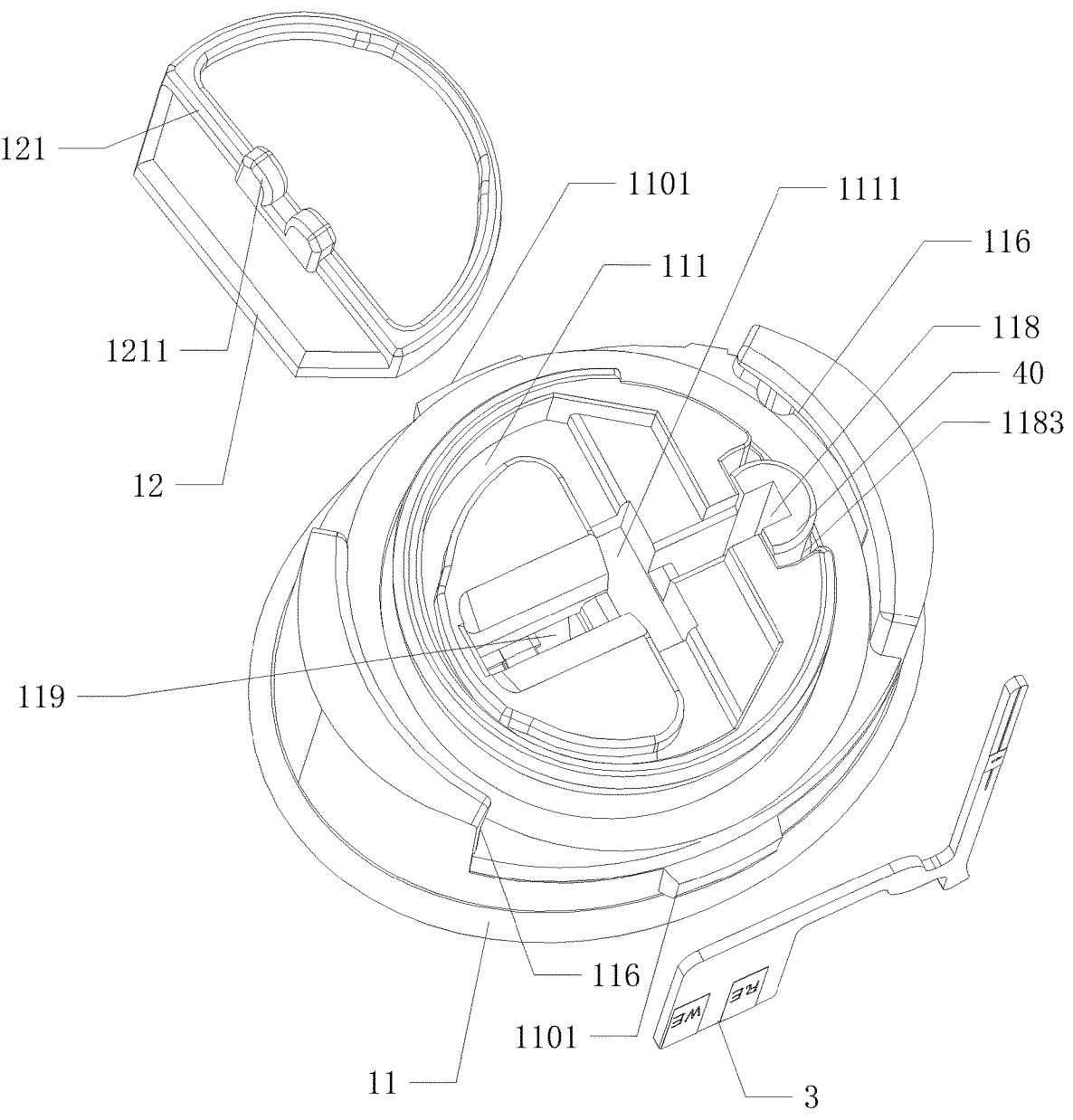
FIG. 10 is a breakdown diagram of a partial structure of a compact implantable biosensor assembly of the invention, in a bottom view.
Figure 11:
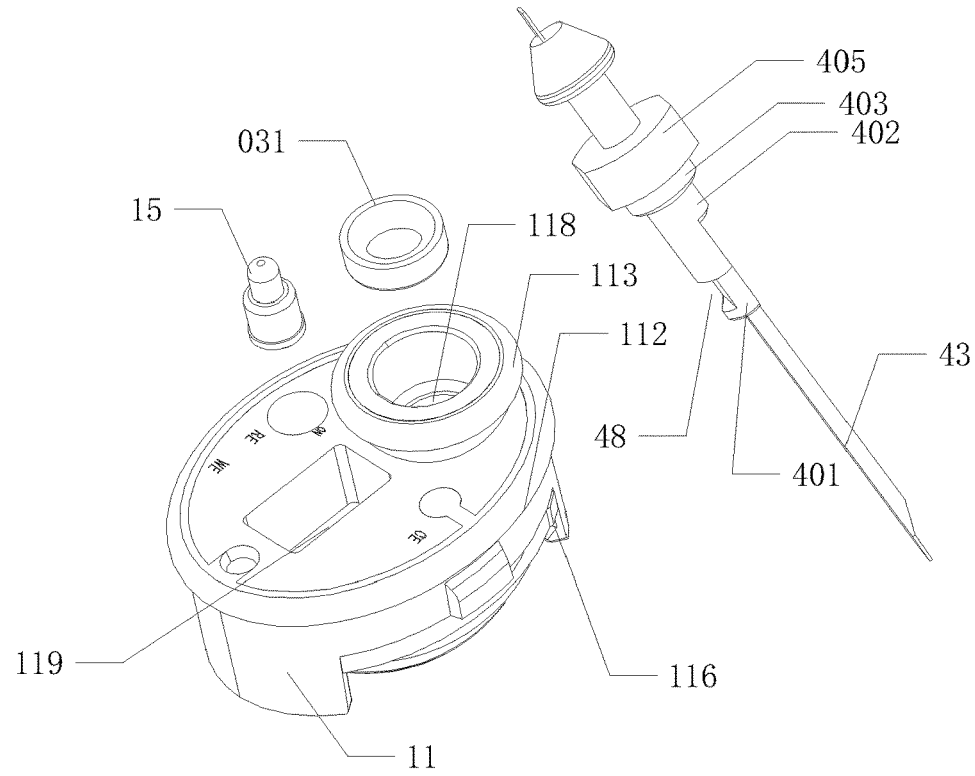
FIG. 11 is a breakdown diagram of a partial structure of a biological information monitoring device of the invention, including a needle aid, an upper housing and a spring pin.
Figure 12:
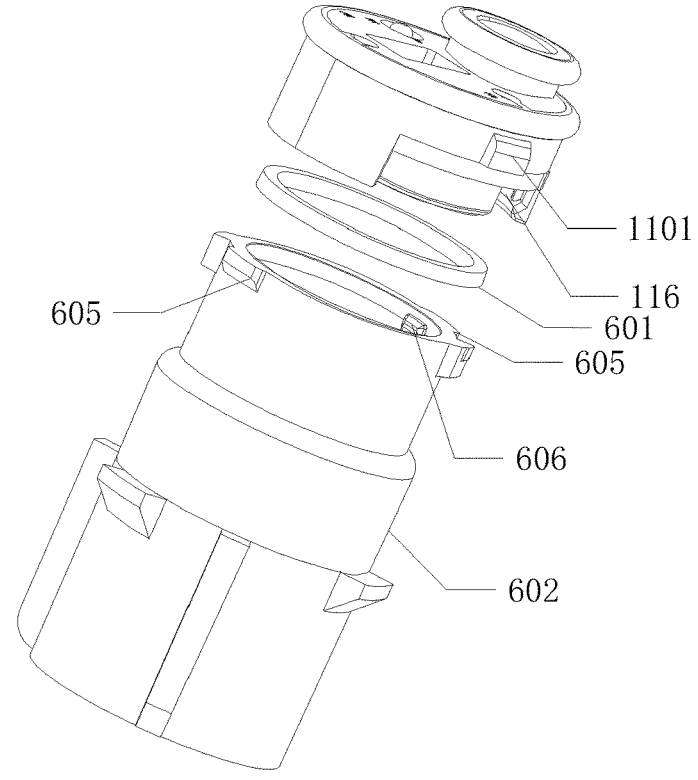
FIG. 12 is a structural diagram of a barrier fitting with an upper housing of a compact implantable biosensor assembly of the invention.
Figure 13:
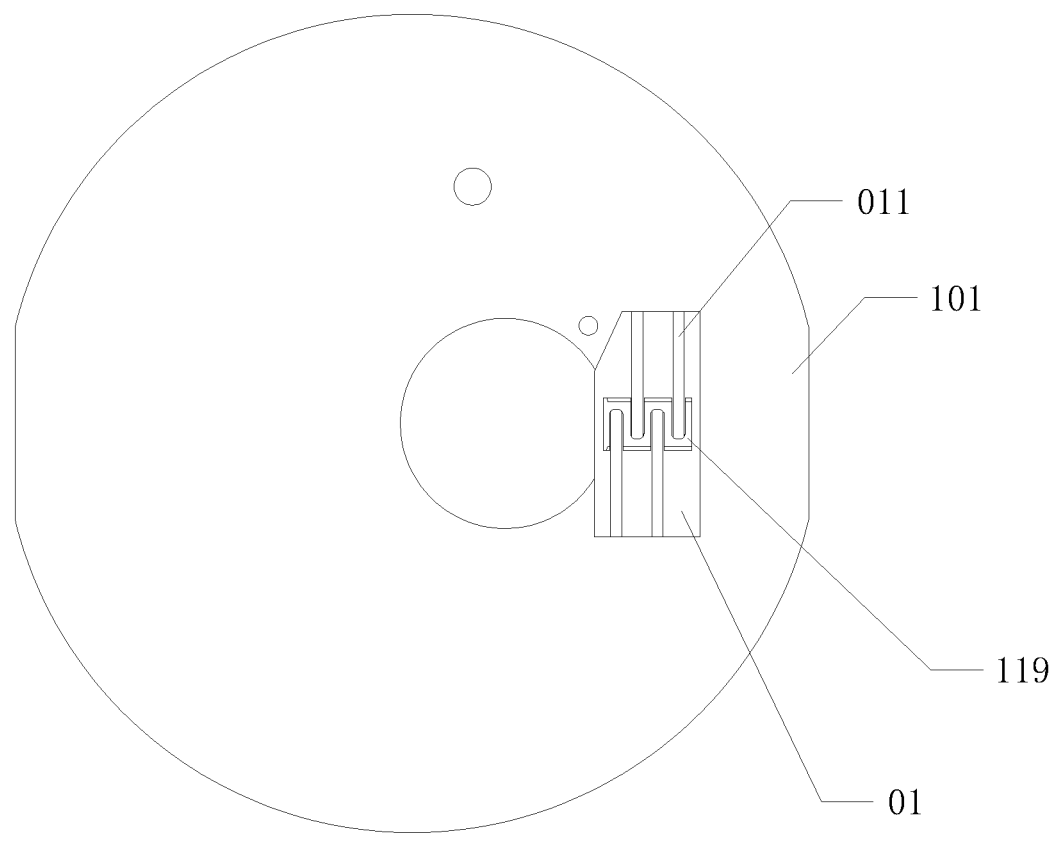
FIG. 13 is a structural diagram of a circuit board of another embodiment of a biological information monitoring device of the invention, wherein connecting sheets or first contacts are staggered.

The following is a further description of a compact implantable biosensor assembly of the invention with reference to FIGS. 1 to 13.

A compact implantable biosensor assembly comprises an enclosure 1, an implantable sensing electrode 3, a needle aid 4 and a barrier 6.

The implantable sensing electrode 3 comprises a first wide vertical section 31, a horizontal connection section 32, and an implanted sensing section 33. The two sides of the horizontal connection section 32 are respectively connected with the lower end of the first wide vertical section 31 and the upper end of the implanted sensing section 33. The surface of the first wide vertical section 31 is provided with an export electrode 311. The needle aid 4 comprises a needle seat 40, and a needle 43 for implantation.

The lower part of the implanted sensing section 33 and of the needle 43 for implantation are sealed in a closed space formed by the barrier 6, the lower section of the enclosure 1 and the lower section of the needle aid 4. The horizontal connection section 32 of the implantable sensing electrode 3 is embedded in the enclosure 1.

The export electrode 311 is exposed on the surface of the enclosure 1, and the export electrode 311 is used to connect with the transmitter 10; or, the export electrode 311 is exposed on the bottom surface of the upper counterbore on the enclosure 1, and the export electrode 311 is used to connect with a transmitter 10.

The enclosure 1 is provided with an assembly structure 110 for engaging with the transmitter 10.

The transmitter 10 comprises a main control circuit board 101, a main support structure 105 and an upper cover 106. The assembly structure 110 comprises two assembly projections 1101. Two assembly pits 1021 are provided in the assembly through-hole 102 of the main support structure 105. The assembly projections 1101 are snap-fitted into assembly pits 1021 to realize the assembly.

In this embodiment, the horizontal connection section 32 comprises a first horizontal flat section 321 and an upwardly bending connection section 322 which are connected with each other.

The left side of the first horizontal flat section 321 is connected to the lower section of the right side of the first wide vertical section 31, and the upwardly bending connection section 322 is connected to the left side of the implanted sensing segment 33 near the upper end.

In this embodiment, the upper right end of the implanted sensing segment 33 is provided with a bump 331; or there is no bump 331 at the upper right end of the implanted sensing segment 33, and a pressure contact bump 431 is provided in the part where the needle 43 for implantation contacts the upper right end of the implanted sensing segment 33.

In this embodiment, the section of the puncture part of the needle 43 for implantation is C-shaped $\mathbf{d}^{\boxed{11}}$ -shaped. After assembly, the implanted sensing segment 33 is contained inside the C-shape or in the recess in th$\boxed{11}$ -shape.

The upper right end of the implanted sensing section 33 is provided with a bump 331, which is pressed against the inner wall of the needle 43 for implantation so as to deform the implanted sensing section 33 with the upwardly bending connection section 322 as the fulcrum; the lower end of the implanted sensing section 33 is contained inside the C-shape or in the recess in the$\boxed{11}$ -shape of the needle 43 for implantation and would not stick out of the lower end of the needle 43 for implantation; or the pressure contact bump 431 is pressed against the upper right end of the implanted sensing section 33 so as to deform the implanted sensing section 33 with the upwardly bending connection section

322 as the fulcrum; the lower end of the implanted sensing section 33 is contained inside the C-shape or in the recess in th$\boxed{11}$ -shape of the needle 43 for implantation and would not stick out of the lower end of the needle 43 for implantation.

In this embodiment, the enclosure 1 comprises an upper housing 11 and a lower housing 12. The lower housing 12 covers the bottom of the upper housing 11.

The upper housing 11 is provided with a needle aid guide hole 118 and an electrode guide slot 119. The needle aid guide hole 118 and the electrode guide slot 119 are in communication in the lower part of the upper housing 11. The needle 43 for implantation passes through the needle aid guide hole 118 from the upper part of the needle aid guide hole 118 and sticks out downward. The needle aid guide hole 118 is arranged beside the lower housing 12.

The electrode guide slot 119 is arranged above the lower housing 12, wherein its lower section is narrow, and its upper section is provided with a counterbore and is a wide structure.

The horizontal part of the implantable sensing electrode 3 extends out from the needle aid guide hole 118, passes through the junction between the lower housing 12 and the upper housing 11 and enters the space between the lower housing 12 and the upper housing 11. The first wide vertical section 31 passes through the electrode guide slot 119 from the lower part of the electrode guide slot 119 and sticks out upward. The electrode guide slot 119 is narrow in the lower part and wide in the upper part. The width of the narrow lower part is 0.1~0.3 mm larger than the thickness of the first vertical section 31 of the electrode, for glue sealing. The upper wide part provides space for the bent part of the connector 01 or connecting sheet 02, and its size is adapted to the connector 01 or connecting sheet 02 fitted on the transmitter 10.

The lower part of the first vertical section 31 of the implantable sensing electrode 3 and the lower narrow section of the electrode guide slot 119 are sealed by glue to form a sealed structure. The lower part of the first vertical section 31 of the electrode is provided with a through-hole structure or a toothed edge structure, which is used for reliable bonding and sealing with glue.

The horizontal part of the implantable sensing electrode 3 is sealed with glue at the junction between the lower housing 12 and the upper housing 11. The lower narrow part of the electrode guide slot and the lower part of the first wide vertical section 31 of the electrode are sealed with glue.

The function of the electrode guide slot 119 comprises the avoidance of the upper counterbore, the electrode positioning and glue sealing of the lower narrow structure, etc.

In this embodiment, the lower part of the upper housing 11 is provided with a recessed edge 111. Part of the recessed edge 111 is provided with a deep glue-dispensing sub-slot 1111. The upper part of the lower housing 12 is provided with a protruding edge 121, and the protruding edge 121 is provided with two adjacent engagement protuberances 1211.

Sealing glue is provided in the recessed edge 111 and the glue-dispensing sub-slot 1111. The two engagement protuberances 1211 are inserted into the glue-dispensing sub-slot 1111. The horizontal part of the implantable sensing electrode 3 passes between the two engagement protuberances 1211. The protruding edge 121 is clamped into the recessed edge 111. After the sealing glue is solidified, the horizontal part of the implantable sensing electrode 3 is sealed by the sealing glue at the junction of the lower housing 12 and the upper housing 11, and the lower housing 12 and the upper housing 11 are sealed. The lower part of the first vertical section 31 of the implantable sensing electrode 3 and the lower narrow section of the electrode guide slot 119 are sealed by glue to form a sealed structure. The lower part of the first vertical section 31 of the electrode is provided with a through-hole structure and/or a toothed edge structure, which is used for reliable bonding and sealing with glue.

In this embodiment, the needle aid guide hole 118 is provided with three steps. The lower part of the upper step and the middle step are circular holes respectively. The step surface of the circular hole of the middle step is provided with a first seal ring 031, and at the bottom of the lower step is a notched arched hole 1183.

The lower part of the needle seat is provided with an arched section 401 with an opening which is adapted to the notched arched hole 1183. Above the arched section 401 with an opening is a part 402 adapted to the seal ring. The part 402 adapted to the seal ring is sleeved inside the first seal ring 031. Above the part 402 adapted to the seal ring is a vertical guide part 403. The vertical guide part 403 is adapted to and clearance fits with the circular hole in the lower part of the upper step surface. Above the vertical guide part 403 is an upper boss 405. The bottom surface of the upper boss 405 is on the top surface of the upper step.

Barrier 6 comprises a rubber plug 603, a barrier main housing 602 and a barrier seal ring 601. The barrier seal ring 601 is provided at an end of the main barrier housing 602, and is integrally formed by bi-color injection molding. The lower part of the barrier main housing 602 fits with the rubber plug 603. The rubber plug 603 is made of soft rubber, and the rubber plug 603 is inserted into the lower part of the barrier main housing 602 and squeezes to form a seal.

The barrier 6 as a whole is hollow cylinder-shaped. The upper outer side of barrier 6 is provided with symmetrical ring-in engagement protuberances 605, and the upper inner side of barrier 6 is provided with an inner engagement protuberance 606. The outer ring-in engagement protuberances 605 of the barrier 6 respectively engage with the engagement slots 116 at the bottom of the enclosure 1, while the inner engagement protuberance of the barrier 6 engages with the engagement recess 48 of the needle seat 40 of the needle aid. The engagement of the barrier 6 with the enclosure 1 and the needle aid 4 is detachable. The engagement or disengagement can be achieved by rotating the barrier 6. The upper part of the barrier 6 is provided with a barrier seal ring 601. The barrier seal ring 601 and the barrier 6 are integrally formed by bi-color injection molding. When the barrier 6 is engaged through rotation, the barrier seal ring 601 is squeezed between the lower part of the lower housing 12 and the upper part of the barrier 6 to form a seal.

The seal ring 4 is placed on the first step from top to bottom, and the second step cooperates with the fool-proof surface of the needle aid to effectively prevent the rotation of the needle aid.

The enclosure 1 comprises an upper housing 11 and a lower housing 12, and the lower housing 12 covers the lower part of the upper housing 11.

The invention also provides a biological information monitoring device.

A biological information monitoring device, comprising a transmitter 10 and a compact implantable biosensor assembly;

the transmitter 10 is provided with an assembly through-hole 102; the compact implantable biosensor assembly detachably passes through the assembly through-hole 102 and is engaged with the assembly through-hole 102; the transmitter 10 is provided with a main control circuit board 101; the main control circuit board 101 is provided with an electrode through-hole 1011; the upper part of the first wide vertical section 31 passes through or approaches the electrode through-hole 1011; a signal input and output end of the main control circuit board 101 is in communication with the export electrode 311.

The compact implantable biosensor assembly comprises an enclosure 1, an implantable sensing electrode 3, a needle aid 4 and a barrier 6.

The implantable sensing electrode 3 comprises a first wide vertical section 31, a horizontal connection section 32, and an implanted sensing section 33. The two sides of the horizontal connection section 32 are respectively connected with the lower end of the first wide vertical section 31 and the upper end of the implanted sensing section 33. The surface of the first wide vertical section 31 is provided with an export electrode 311. The needle aid 4 comprises a needle seat 40, and a needle 43 for implantation.

The lower part of the implanted sensing section 33 and of the needle 43 for implantation are sealed in a closed space formed by the barrier 6, the lower section of the enclosure 1 and the lower section of the needle aid 4. The horizontal connection section 32 of the implantable sensing electrode 3 is embedded in the enclosure 1.

The export electrode 311 is exposed on the surface of the enclosure 1, and the export electrode 311 is used to connect with the transmitter 10; or, the export electrode 311 is exposed on the bottom surface of the upper counterbore on the enclosure 1, and the export electrode 311 is used to connect with a transmitter 10.

The enclosure 1 is provided with an assembly structure 110 for engaging with the transmitter 10.

In this embodiment, the horizontal connection section 32 comprises a first horizontal flat section 321 and an upwardly bending connection section 322 which are connected with each other.

The left side of the first horizontal flat section 321 is connected to the lower section of the right side of the first wide vertical section 31, and the upwardly bending connection section 322 is connected to the left side of the implanted sensing segment 33 near the upper end.

In this embodiment, the upper right end of the implanted sensing section 33 is provided with a bump 331; or there is no bump 331 at the upper right end of the implanted sensing section 33, and a pressure contact bump 431 is provided in the part where the needle 43 for implantation contacts the upper right end of the implanted sensing section 33.

In this embodiment, the section of the puncture part of the needle 43 for implantation is C-shaped d$^{[1]}$ -shaped. After assembly, the implanted sensing segment 33 is contained inside the C-shape or in the recess in th$^{[1]}$ -shape.

The upper right end of the implanted sensing section 33 is provided with a bump 331, which is pressed against the inner wall of the needle 43 for implantation so as to deform the implanted sensing section 33 with the upwardly bending connection section 322 as the fulcrum; the lower end of the implanted sensing section 33 is contained inside the C-shape or in the recess in th$^{[1]}$ -shape of the needle 43 for implantation and would not stick out of the lower end of the needle 43 for implantation; or the pressure contact bump 431 is pressed against the upper right end of the implanted sensing section 33 so as to deform the implanted sensing section 33 with the upwardly bending connection section 322 as the fulcrum; the lower end of the implanted sensing section 33 is contained inside the C-shape or in the recess in the ［凵］ -shape of the needle 43 for implantation and would not stick out of the lower end of the needle 43 for implantation.

In this embodiment, the enclosure 1 comprises an upper housing 11 and a lower housing 12. The lower housing 12 covers the bottom of the upper housing 11.

The upper housing 11 is provided with a needle aid guide hole 118 and an electrode guide slot 119. The needle 43 for implantation passes through the needle aid guide hole 118 from the upper part of the needle aid guide hole 118 and sticks out downward. The needle aid guide hole 118 is arranged beside the lower housing 12.

The electrode guide slot 119 is arranged above the lower housing 12.

The horizontal part of the implantable sensing electrode 3 extends out from the needle aid guide hole 118, passes through the junction between the lower housing 12 and the upper housing 11 and enters the space between the lower housing 12 and the upper housing 11. The first wide vertical section 31 passes through the electrode guide slot 119 from the lower part of the electrode guide slot 119 and sticks out upward.

The horizontal part of the implantable sensing electrode 3 is sealed with glue at the junction between the lower housing 12 and the upper housing 11.

The function of the electrode guide slot 119 is the function of the upper counterbore.

In this embodiment, the lower part of the upper housing 11 is provided with a recessed edge 111. Part of the recessed edge 111 is provided with a deep glue-dispensing sub-slot 1111. The upper part of the lower housing 12 is provided with a protruding edge 121, and the protruding edge 121 is provided with two adjacent engagement protuberances 1211.

Sealing glue is provided in the recessed edge 111 and the glue-dispensing sub-slot 1111. The two engagement protuberances 1211 are inserted into the glue-dispensing sub-slot 1111. The horizontal part of the implantable sensing electrode 3 passes between the two engagement protuberances 1211. The protruding edge 121 is clamped into the recessed edge 111. After the sealing glue is solidified, the horizontal part of the implantable sensing electrode 3 is sealed by the sealing glue at the junction of the lower housing 12 and the upper housing 11, and the lower housing 12 and the upper housing 11 are sealed.

In this embodiment, the needle aid guide hole 118 is provided with three steps. The upper step is in the upper part of the upper housing 11, and the lower step is in the lower part of the upper housing 11. The lower part of the upper step and the middle step are circular holes respectively. The step surface of the circular hole of the middle step is provided with a first seal ring 031, and at the bottom of the lower step is a notched arched hole 1183. The upper periphery of the upper housing 11 is provided with a second seal ring 112, and the edge of the upper step surface is provided with a third seal ring 113.

The lower part of the needle seat is provided with an arched section 401 with an opening which is adapted to the notched arched hole 1183. Above the arched section 401 with an opening is a part 402 adapted to the seal ring. The part 402 adapted to the seal ring is sleeved inside the first seal ring 031. Above the part 402 adapted to the seal ring is a vertical guide part 403. The vertical guide part 403 is adapted to and clearance fits with the circular hole in the lower part of the upper step surface. Above the vertical guide part 403 is an upper boss 405. The bottom surface of the upper boss 405 is on the top surface of the upper step.

In this embodiment, it also includes connector 01, part of which is connected to the main control circuit board 101. As an alternative, the connector 01 is integrally formed with the main control circuit 101 through FPC flexible board process or rigid-flexible combined board process.

The connector 01 is provided with a plurality of first contacts 011, which are arranged on the left and right sides. The gap distance between the first contacts 011 arranged on both sides is less than the thickness of the first wide vertical section 31. The first contacts 011 are arranged on the electrode through-hole 1011.

The first wide vertical section 31 passes through the gap between the first contacts 011 arranged on both sides. The first contacts 011 arranged on both sides squeeze the first wide vertical section 31 from both sides. At least part of the first contacts 011 squeezes the export electrode 311. The export electrode 311 is electrically connected to the signal input and output end of the main control circuit board 101 through the first contacts 011.

The first contacts 011 will be squeezed and deformed, and the first wide vertical section 31 will also be squeezed and slightly deformed, realizing the signal communication between the transmitter 10 and the compact implantable biosensor assembly.

In this embodiment, the first contacts 011 arranged on both sides are symmetrically arranged on both sides; or
the first contacts 011 arranged on both sides are staggered on both sides.

Compared with the first contacts 011 arranged symmetrically, the first contacts 011 staggered on both sides may be longer, the gap between the two sides is smaller, the bending of the first contacts 011 is longer after the first wide vertical section 31 is inserted into the gap, and the contact (point contact, line contact or surface contact) between the first contacts 011 and the export electrode 311 is more reliable.

In this embodiment, it further includes a connecting sheet 02.

There are two or more connecting sheets 02. One end of the connecting sheets 02 is connected to the main control circuit board 101, and the other end of the connecting sheets 02 is pressed against the surface of the export electrode 311.

The connecting sheets 02 have certain rigidity and elasticity, such as bending a copper sheet, stainless steel sheet, etc. into the shape of an elastic sheet. The first wide vertical section 31 sticks out from a side of the connecting sheets 02 or from the gap between the connecting sheets 02 on both sides. The connecting sheets 02 can effectively squeeze or clamp the export electrode 311. The elasticity and rigidity of the connecting sheets 02 make the connection at the connection point between the connecting sheets 02 and the export electrode 311 more reliable.

In order to facilitate welding, the surface of the conductive part of the connecting sheets 02 or connectors 01 needs to have a weldable plating, such as nickel, gold, etc. In order to ensure welding consistency, the welding end at the end of the connectors 02 will be welded through the through-hole of the weld leg of the main control circuit board 101, and the welding end of the plane is welded with the surface welding point of the main control circuit board 101.

In this embodiment, while the compact implantable biosensor assembly engages with the assembly through-hole 102, the spring pin 15 provided on the enclosure 1 is inserted into the power switch hole 103 of the transmitter 10.

In the initial state, the conductive material on the inner wall of the power switch hole 103 is divided into a left semicircle and a right semicircle. The left semicircle and the right semicircle are completely disconnected. After the spring pin 15 is inserted into the power switch hole 103, the spring pin 15 is compressed and reliably connects the left semicircle and the right semicircle, realizing the electrification of the entire system circuit.

The spring pin may also be other equivalent conductors.

In this embodiment, the surface of the first wide vertical section 31 on both sides is provided with an export electrode 311. There are three or more export electrodes 311.

The two sides of the implanted sensing section 33 are provided with a working electrode, a reference electrode and a counter electrode. There are three or more export electrodes 311. The working electrode, reference electrode and counter electrode are connected respectively with different export electrodes 311 through the lines of the implantable sensing electrode 3. The working electrode, reference electrode and counter electrode are connected with the signal input and output end of the main control circuit board 101 through the export electrodes 311 respectively.

The lower part of the implanted sensing section and of the needle for implantation are sealed in a closed space formed by the barrier, the lower part of the enclosure and the lower part of the needle aid. The sealed space constitutes a small sterile unit. Since the sterile unit is small, it can improve the productivity and reduce the production cost. The transmitter does not consume or consumes a tiny amount of electricity before implantation into the human body, so the shelf life of the transmitter can be increased.

The above is only a preferred embodiment of the invention. It should be pointed out that for those skilled in the art, several improvements can be made without departing from the principle of the invention. These improvements should also be considered as the protection scope of the invention.

The invention claimed is:

1. A compact implantable biosensor assembly, comprising:

an enclosure (1) comprising an upper housing (11) for engaging with a transmitter (10) and a lower housing (12); wherein the lower housing (12) covers a lower part of the upper housing (11), away from the transmitter (10);

an implantable sensing electrode (3) comprising, sequentially in a direction away from the transmitter (10), a first section (31), a connection section (32), and an implanted sensing section (33), wherein the connection section (32) is connected between the first section (31) and the implanted sensing section (33), and a surface of the first section (31) is provided with a plurality of export electrodes (311) configured to electrically connect to the transmitter (10);

a needle aid (4) comprising a needle seat (40) and an implantation needle (43); and a barrier (6);

wherein:

the upper housing (11) is provided with a needle aid guide hole (118) and an electrode guide slot (119) in communication with each other in the lower part of the upper housing (11), and an assembly structure (110) for engaging with the transmitter (10);

the implantation needle (43) passes through the needle aid guide hole (118);

the electrode guide slot (119) is disposed above the lower housing (12);

the implanted sensing section (33) extends from the needle aid guide hole (118), passes through a junction between the lower housing (12) and the upper housing (11), and enters a space between the lower housing (12) and the upper housing (11);

the first section (31) passes through the electrode guide slot (119) and extends upward away from the lower housing (12);

the connection section (32) extends from the electrode guide slot (119) to the needle aid guide hole (118), and the implantable sensing electrode (3) is sealed at the junction between the lower housing (12) and the upper housing (11);

the needle aid guide hole (118) comprises three stepped portions, including an upper step located in an upper part of the upper housing (11) proximate to the transmitter (10), a middle step, and a lower step located in the lower part of the upper housing (11);

the upper step and the middle step each comprise a circular hole;

a step surface of the circular hole of the middle step is provided with a first seal ring (031);

a bottom of the lower step is configured as a notched arched hole (1183);

the needle seat (40) comprises, sequentially in a direction towards the transmitter (10): an arched section (401) corresponding to the notched arched hole (1183); a seal ring-adapted part (402), above the arched section (401), sleeved inside the first seal ring (031); a guide part (403), above the seal ring-adapted part (402), clearance-fitting with the circular hole of the upper step; and an upper boss (405), above the guide part (403), with a bottom surface of the upper boss (405) resting on a top surface of the upper step; and the barrier (6) is sealed with a lower part of the lower housing (12) to form a closed space to receive the implanted sensing section (33) and the implantation needle (43).

2. The compact implantable biosensor assembly of claim 1, wherein the connection section (32) comprises a first flat section (321) extending in a direction from first section (31) to the implanted sensing section (33), and a bending connection section (322) bending from an end of the first flat section (321) and extending upward away from the lower housing (12), wherein the bending connection section (322) is connected between the first flat section (321) and the implanted sensing section (33).

3. The compact implantable biosensor assembly of claim 2, wherein:

a bump (331) is provided at an upper end of the implanted sensing section (33), proximate to the upper housing, and contacts with the implantation needle (43).

4. The compact implantable biosensor assembly of claim 3, wherein a cross-sectional shape of a puncture portion of the implantation needle (43) is C-shaped;

and wherein after assembly, the implanted sensing section (33) is contained inside the C-shape.

5. The compact implantable biosensor assembly of claim 1, wherein, the transmitter (10) comprises a connector (01), a lower part of the electrode guide slot (119) proximate to the lower housing, has a width of 0.1 mm to 0.3 mm greater than a thickness of the first section (31), and is sealed to a lower part of the first section (31) proximate to the lower housing; and the lower part of the first section (31) is provided with a through-hole structure or a toothed edge structure.

6. The compact implantable biosensor assembly of claim 1, wherein:

the lower part of the upper housing (11) is provided with a recessed edge (111);

a portion of the recessed edge (111) is further recessed with a glue-dispensing sub-slot (1111), an upper part of the lower housing (12) proximate to the upper housing is provided with a protruding edge (121) having two adjacent engagement protuberances (1211) inserted into the glue-dispensing sub-slot (1111), the protruding edge (121) is fitted into the recessed edge (111), with a sealing glue provided in the recessed edge (111) and the glue-dispensing sub-slot (1111);

a portion of the implantable sensing electrode (3) passes between the two engagement protuberances (1211), the portion of the implantable sensing electrode (3) is sealed at the junction between the lower housing (12) and the upper housing (11), and the lower housing (12) and the upper housing (11) are sealed together.

7. The compact implantable biosensor assembly of claim 1, wherein the export electrodes (311) are exposed on a surface of the enclosure (1) for connection with the transmitter (10).

8. A biological information monitoring device, comprising:

a transmitter (10) having an assembly through-hole (102) and a main control circuit board (101) with an electrode through-hole (1011); and the compact implantable biosensor assembly of claim 1; wherein:

the compact implantable biosensor assembly is detachably inserted through and engaged with the assembly through-hole (102);

an upper part of the first section (31) proximate to the transmitter passes through the electrode through-hole (1011); and a signal input/output terminal of the main control circuit board (101) is electrically connected to the plurality of export electrodes (311).

9. The biological information monitoring device of claim 8, further comprising at least two connecting sheets (02), each having one end connected to the main control circuit board (101) and an opposite end pressed against a surface of the export electrodes (311).

10. The biological information monitoring device of claim 8, wherein the enclosure (1) further comprises a spring pin (15) inserted into a power switch hole (103) of the transmitter (10) when the biosensor assembly is engaged with the assembly through-hole (102).

11. The biological information monitoring device of claim 10, wherein:

an inner wall of the power switch hole (103) comprises a conductive material divided into a first semicircle and a second semicircle that are electrically disconnected in an initial state; and wherein insertion of the spring pin (15) into the power switch hole (103) causes the spring pin (15) to be compressed and to electrically connect the first semicircle and the second semicircle.

12. The biological information monitoring device of claim 8, wherein:

the plurality of export electrodes (311) comprises three or more export electrodes disposed on one or both sides of the first section (31);

the implanted sensing section (33) comprises a working electrode, a reference electrode, and a counter electrode; and each of the working electrode, reference electrode, and counter electrode is connected to a respective one of the export electrodes (311) via traces of the implantable sensing electrode (3).

* * * * *